US009914746B2

(12) United States Patent
Sproat

(10) Patent No.: US 9,914,746 B2
(45) Date of Patent: *Mar. 13, 2018

(54) OLIGONUCLEOTIDES CONTAINING HIGH CONCENTRATIONS OF GUANINE MONOMERS

(71) Applicant: KUROS BIOSCIENCES AG, Zurich-Schlieren (CH)

(72) Inventor: Brian Stephen Sproat, Booischot (BE)

(73) Assignee: KUROS BIOSCIENCES AG, Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/748,045

(22) Filed: Jun. 23, 2015

(65) Prior Publication Data
US 2016/0145293 A1 May 26, 2016

Related U.S. Application Data

(63) Continuation of application No. 14/054,068, filed on Oct. 15, 2013, now abandoned, which is a continuation of application No. 11/954,511, filed on Dec. 12, 2007, now Pat. No. 8,586,728.

(60) Provisional application No. 60/869,588, filed on Dec. 12, 2006.

(51) Int. Cl.
C07H 1/00 (2006.01)
C07H 1/06 (2006.01)
C07H 21/00 (2006.01)
C07H 21/02 (2006.01)

(52) U.S. Cl.
CPC .............. *C07H 21/00* (2013.01); *C07H 1/00* (2013.01); *C07H 1/06* (2013.01); *C07H 21/02* (2013.01)

(58) Field of Classification Search
None
See application file for complete search history.

(56) References Cited

U.S. PATENT DOCUMENTS

| 6,541,438 | B1 | 4/2003 | Smets et al. | |
|---|---|---|---|---|
| 6,719,978 | B2 | 4/2004 | Schiller et al. | |
| 6,949,520 | B1 | 9/2005 | Hartmann et al. | |
| 7,271,156 | B2 | 9/2007 | Krieg et al. | |
| 7,348,391 | B2 * | 3/2008 | Ravikumar et al. | 526/336 |
| 7,517,520 | B2 | 4/2009 | Manolova et al. | |
| 7,537,767 | B2 | 5/2009 | Bachmann et al. | |
| 7,943,758 | B2 | 5/2011 | Sekine et al. | |
| 2003/0050263 | A1 | 3/2003 | Ksieg et al. | |
| 2003/0050268 | A1 | 3/2003 | Krieg et al. | |
| 2003/0091593 | A1 | 5/2003 | Bachmann et al. | |
| 2003/0099668 | A1 | 5/2003 | Bachmann et al. | |
| 2004/0005338 | A1 | 1/2004 | Bachmann et al. | |
| 2005/0287555 | A1 | 12/2005 | Dellinger et al. | |
| 2006/0204475 | A1 | 9/2006 | Bachmann et al. | |
| 2006/0210588 | A1 | 9/2006 | Bachmann et al. | |
| 2006/0251623 | A1 | 11/2006 | Bachmann et al. | |
| 2006/0251677 | A1 | 11/2006 | Bachmann et al. | |
| 2007/0184068 | A1 | 8/2007 | Renner et al. | |
| 2008/0039620 | A1 | 2/2008 | Sekine et al. | |
| 2008/0292652 | A1 | 11/2008 | Bachmann et al. | |

FOREIGN PATENT DOCUMENTS

| EP | 1 717 243 | | 4/2006 |
|---|---|---|---|
| EP | 1 719 778 | | 8/2006 |
| EP | 1717243 | A1 * | 11/2006 |
| EP | 1719778 | A1 * | 11/2006 |
| WO | WO84/04749 | A1 | 12/1984 |
| WO | WO98/16247 | | 4/1998 |
| WO | WO98/49195 | | 11/1998 |
| WO | WO98/50071 | A1 | 11/1998 |
| WO | WO99/29723 | | 6/1999 |
| WO | WO00/23955 | A1 | 4/2000 |
| WO | WO00/32227 | A2 | 6/2000 |
| WO | WO00/46365 | | 8/2000 |
| WO | WO00/50006 | | 8/2000 |
| WO | WO01/22972 | A2 | 4/2001 |
| WO | WO01/22990 | A2 | 4/2001 |
| WO | WO01/26681 | A2 | 4/2001 |
| WO | WO01/38358 | A2 | 5/2001 |
| WO | WO01/54720 | A1 | 8/2001 |
| WO | WO01/62275 | A1 | 8/2001 |
| WO | WO02/053141 | A2 | 7/2002 |
| WO | WO03/024480 | A2 | 3/2003 |
| WO | WO03/024481 | A2 | 3/2003 |
| WO | WO2004/000351 | A1 | 12/2003 |
| WO | WO2004/084940 | A1 | 10/2004 |
| WO | WO2005/004907 | | 1/2005 |

(Continued)

OTHER PUBLICATIONS

Gerstner et al., Nucleic Acid Research, 1995, 23(12), 2292-2299.*
Baker, D., et al., "Protein structure prediction and structural genomics.", Science 2001, pp. 93-96, vol. 294, Issue 554, American Association for the Advancement of Science, US.
Braun, H., et al., "Oligonucleotide and plasmid DNA packaging into polyoma VP1 virus-like particles expressed in *Escherichia coli*.", Biotechnol Appl Biochem, 1999, pp. 31-43, vol. 29, Academic Press, US.
Costa, L. T., et al., "Structural studies of oligonucleotides containing G-quadruplex motifs using AFM.", Biochem Biophys Res Commun, 2004, pp. 1065-1072, vol. 313, Issue 4, Academic Press, US.
Gerber, S., et al., "Human papillomavirus virus-like particles are efficient oral immunogens when coadministered with *Escherichia coli* heat-labile enterotoxin mutant R192G or CpG DNA.", J Virol, 2001, pp. 4752-4760, vol. 75, Issue 10, American Society for Microbiology, US.

(Continued)

*Primary Examiner* — Layla D Berry
(74) *Attorney, Agent, or Firm* — Medler Ferro Woodhouse & Mills PLLC

(57) ABSTRACT

This invention pertains to methods for oligonucleotide synthesis, specifically the synthesis of oligonucleotides that contain a high content of guanine monomers. In more detail, the invention relates to a method for coupling a nucleoside phosphoramidite during the synthesis of an oligonucleotide to a universal support, to a first nucleoside, or to an extending oligonucleotide. The invention further relates to oligonucleotides obtainable by the methods of the invention.

20 Claims, No Drawings

(56) References Cited

FOREIGN PATENT DOCUMENTS

| WO | WO2005/014110 | | 2/2005 |
|---|---|---|---|
| WO | WO 2005014110 A1 | * | 2/2005 |
| WO | WO2005/080411 A1 | | 9/2005 |
| WO | WO2006/032674 A1 | | 3/2006 |
| WO | WO2007/068747 A1 | | 6/2007 |

OTHER PUBLICATIONS

Goldmann, C., et al., "Packaging of small molecules into VP1-virus-like particles of the human polyomavirus JC virus.", J Virol Methods, 2000, pp. 85-90, vol. 90, Issue 1, Elsevier, NL.

Hill, A. V. S., et al., "DNA-based vaccines for malaria: a heterologous prime-boost immunisation strategy.", Dev Biol Basel, 2000, pp. 171-179, vol. 104, Karger, CH.

Iho, S., et al., "Oligodeoxynucleotides containing palindrome sequences with internal 5'-CpG-3' act directly on human NK and activated T cells to induce IFN-gamma production in vitro.", J Immunol, 1999, pp. 3642-3652, vol. 163, Issue 7, The American Association of Immunologists, US.

Ioannou, X. P., et al., "CpG-containing oligodeoxynucleotides, in combination with conventional adjuvants, enhance the magnitude and change the bias of the immune responses to a herpesvirus glycoprotein.", Vaccine, 2002, pp. 127-137, vol. 21, Issue 1-2, Elsevier, UK.

Kerkmann, M., et al., "Spontaneous formation of nucleic acid-based nanoparticles is responsible for high interferon-alpha induction by CpG-A in plasmacytoid dendritic cells.", J Biol Chem, 2005, pp. 8086-8093, vol. 280, Issue 9, The American Society for Biochemistry and Molecular Biology, Inc., US.

Klinman, D. M., et al., "Immunotherapeutic applications of CpG-containing oligodeoxynucleotides.", Drug News Perspect, 2000, pp. 289-296, vol. 13, Issue 5, Prous Science, ES.

Krug, A., et al., "Identification of CpG oligonucleotide sequences with high induction of IFN-alpha/beta in plasmacytoid dendritic cells.", Eur J Immunol, 2001, pp. 2154-2163, vol. 31, Issue 7, Wiley-VCH Verlag GmbH, DE.

Kuramoto, E., et al., "Oligonucleotide sequences required for natural killer cell activation.", Jpn J Cancer Res, 1992, pp. 1128-1131, vol. 83, Issue 11, Japanese Cancer Association, JP.

Lu, M., et al., "Structure and stability of sodium and potassium complexes of dT4G4 and dT4G4T.", Biochemistry, 1992, pp. 2455-2459, vol. 31, Issue 9, American Chemical Society, US.

Moore, M.F., "Conceptual Basis of Selective Activation of Bis(dialkylamino)methoxyphophines by Weak Acids and Its Application toward the Preparation of Deoxynucleoside Phosphoramdites in Situ", J. Org. Chem., 1985, pp. 2019-2025, vol. 50, American Chemical Society, US.

Powell, A. T., et al., "Studies on spin labeled ribonucleic acids encapsulated by viral proteins.", Nucleic Acids Res, 1978, pp. 3977-3992, vol. 5, Issue 11, Oxford University Press, UK.

Singh, M., et al., "Advances in vaccine adjuvants.", Nat Biotechnol, 1999, pp. 1075-1081, vol. 17, Issue 11, Nature America Inc, US.

Storni, T., et al., "Nonmethylated CG motifs packaged into virus-like particles induce protective cytotoxic T cell responses in the absence of systemic side effects.", J Immunol, 2004, pp. 1777-1785, vol. 172, Issue 3, The American Association of Immunologists, Inc., US.

Beaucage et al., Current Protocols in Nucleic Acid Chemistry pp. 3.3.1-3.3.20 (2000).

Gerstner et al., "Gram-scale purification of phosphorothioate oligonucleotides using ion-exchange displacement chromatography," Nucleic Acid Research 23(12):2292-2299 (1995), Oxford University Press.

Beaucage, S.L., "Advances in the Synthesis of Oligonucleotides by the Phosphoramidite Approach," Tetrahedron 48(12):2223-2311(1992) UK.

* cited by examiner

OLIGONUCLEOTIDES CONTAINING HIGH CONCENTRATIONS OF GUANINE MONOMERS

CROSS-REFERENCE TO RELATED APPLICATION

The present application claims priority under 35 U.S.C. § 119(e) to U.S. provisional patent application No. 60/869,588 filed 12 Dec. 2006. The entire teachings of the above application are incorporated herein by reference.

FIELD OF THE INVENTION

This invention pertains to methods for oligonucleotide synthesis, specifically the synthesis of oligonucleotides that contain a high content of guanine monomers. In more detail, the invention relates to a method for coupling a nucleoside phosphoramidite during the synthesis of an oligonucleotide to a universal support, to a first nucleoside, or to an extending oligonucleotide. The invention further relates to oligonucleotides obtainable by the methods of the invention.

BACKGROUND OF THE INVENTION

Chemically synthesized DNAs and RNAs ("oligonucleotides") and analogs thereof are used in most molecular biological applications. Methods of oligonucleotide synthesis have been available for over thirty years (see Agarwal et al., Nature, 227:27-34 (1970)), and currently the most common method of oligonucleotide synthesis is through phosphoramidite chemistry (see McBride et al., Tetrahedron Lett, 24:245-248 (1983)).

Phosphoramidite synthesis typically begins with the 3'-most nucleotide and proceeds through a series of cycles composed of four steps that are repeated until the 5'-most nucleotide is attached. However, it is within the ordinary skill of the artisan to establish phosphoramidite synthesis in 5'-3' direction by choosing the first nucleoside and the nucleoside phosphoramidite in the appropriate conformation. The methods disclosed herein are applicable in both directions of synthesis, wherein synthesis in 3'-5' direction is generally preferred.

The four steps are deprotection, coupling, capping and stabilization (generally oxidation or sulfurization). In one variation, during the deprotection step the trityl group attached to the 5%-carbon of the pentose sugar of the recipient nucleotide is removed by trichloroacetic acid (TCA) or dichloroacetic acid (DCA) in a suitable solvent such as dichloromethane or toluene, leaving a reactive hydroxyl group. The next phosphoramidite monomer is added in the coupling step. An activator such as tetrazole, a weak acid, is used to react with the coupling nucleoside phosphoramidite, forming a tetrazolyl phosphoramidite intermediate. This intermediate then reacts with the hydroxyl group of the recipient and the 5' to 3' linkage is formed. The tetrazole is reconstituted and the process continues. A coupling failure results in an oligonucleotide still having a reactive hydroxyl group on the 5'-end. To prevent these oligonucleotides from remaining reactive for the next cycle (which would produce an oligonucleotide with a missing nucleotide), they are removed from further synthesis by being irreversibly capped by an acetylating reagent such as a mixture of acetic anhydride and N-methylimidazole. This reagent reacts only with the free hydroxyl groups to cap the oligonucleotides. In the oxidation step, the phosphate linkage between the growing oligonucleotide and the most recently added nucleotide is stabilized, typically in the presence of iodine as a mild oxidant in tetrahydrofuran (THF) and water. The water acts as the oxygen donor and the iodine forms an adduct with the phosphorous linkage. The adduct is decomposed by the water leaving a stable phospho-triester linkage.

There have been many significant modifications to phosphoramidite synthesis in order to reduce synthesis time and create a higher yield of product. Modified phosphoramidite monomers have been developed that also require additional modifications to synthesis. However, some problems still remain in the synthesis of certain oligonucleotides. One issue has been the synthesis of guanine G-rich oligomers. Oligonucleotides with G-rich regions have been very promising for a variety of applications. G-rich oligonucleotides generally fold into complex structures that have useful applications in molecular biology and medicine. A variety of aptamers have been selected that fold into tightly-packed 4-stranded structures (e.g. thrombin aptamer). The G-rich repeats in nucleic acids form these tetraplexes in the presence of certain monovalent or divalent metal ions with a variety of biological roles (see Deng et al. PNAS (2001), 98, 13665-13670; Jin et al., PNAS (1992). 89, 8832-8836; and Lee, Nucleic Acids Research (1990), 18, 6057-6060).

Purification of such G-rich sequences in the case of DNA is best achieved by anion-exchange purification at pH 12, whereby the thymine and guanine amide functionalities are ionized and unable to participate in structure formation. However, high quality synthesis is difficult depending on the number of contiguous guanine residues, likely due to the poor accessibility of the 5'-hydroxyl group by the activated phosphoramidite in the coupling step.

The support-bound protected G-rich oligomer undergoes some aggregation or has solubility problems in acetonitrile after a certain length or base composition is reached, which is the likely cause of poor accessibility of the 5'-hydroxyl group. Moreover, this will also be related to the nature of the solid-phase support used for the synthesis. Therefore there is a need for a solvent or a solvent mixture that prevents aggregation or resolves solubility issues.

The proposed method provides alternative solvents, particularly polar aprotic solvents during the coupling step to alleviate aggregation or solubility issues with oligomers rich in guanine monomers.

BRIEF SUMMARY OF THE INVENTION

The proposed method provides alternative solvents, particularly polar aprotic solvents during the coupling step to alleviate aggregation or solubility issues with oligomers rich in guanine monomers. The solvents can be added to acetonitrile to provide better solubility for oligomers, particularly oligomers with a high content of guanine residues.

DETAILED DESCRIPTION OF THE INVENTION

The proposed method provides alternative solvents, particularly polar aprotic solvents during the coupling step to alleviate aggregation or solubility issues with oligomers rich in guanine monomers. The polar aprotic solvents disclosed herein can be used alone, in combination with each other or in combination with acetonitrile. The polar aprotic solvents can be added to acetonitrile to provide better solubility for oligomers, particularly oligomers with a high content of guanine residues. Furthermore, the solvents and solvent mixtures disclosed herein provide for a high solubility of the nucleoside phosphoramidite in the coupling solution wherein, in one embodiment, said solubility is at least 0.03 M. In one embodiment, the solvents are added to the mixture of acetonitrile, monomer and activator during the coupling step. The ratio of solvent to acetonitrile can vary. The phosphoramidite monomers can be conventional monomers or modified monomers. In one embodiment, the guanine monomer can be a modified guanine monomer with an acid labile blocking group, or a lipophilic 5'-O-blocking group for the final dG coupling. In one embodiment, the dG monomer used is an isobutyryl guanine with a triisopropylsilyl blocking group.

The proposed methods can be performed with oligonucleotides containing known nucleoside monomers as well as modified nucleoside monomers. The methods could be used in DNA synthesis or RNA synthesis. The proposed methods also enable higher scale production than what would normally be available with conventional anion-exchange HPLC-based purification.

The term "G-rich" or "guanine-rich" refers to oligonucleotides with a high concentration of guanine monomers. In one embodiment, the concentration of guanine residues is great enough to hinder or decrease the solubility of the oligonucleotide, thereby making synthesis difficult and reducing yield or purity of the desired product.

The term "oligonucleotides" refers to synthesized RNA or DNA polymers and their analogs, and is used interchangeably with "oligomers" and "nucleic acids".

Methods for determining the yield of an oligonucleotide synthesis and for determining the purity of an oligonucleotide are generally known in the art. When reference is made to the yield of a method of the invention, said yield can be determined as disclosed in Example 7. Similarly, when reference is made to the purity of an oligonucleotide, said purity can be determined as disclosed in Example 7.

In one aspect, the invention provides a method for coupling a nucleoside phosphoramidite during synthesis of an oligonucleotide, said method comprising combining an activating reagent with one or more polar aprotic solvents for a coupling mixture. In another embodiment the polar aprotic solvent is sulfolane. In a further embodiment the polar aprotic solvent is 1-methylpyrrolidin-2-one. In a further embodiment the polar aprotic solvent is N,N-dimethylacetamide. In a further embodiment the polar aprotic solvent is tetramethylurea. In a further embodiment the activating reagent and the polar aprotic solvent are combined with acetonitrile. In a further embodiment the oligonucleotide is comprised of greater than 30% guanine monomers. In a further embodiment the oligonucleotide is comprised of greater than 50% guanine monomers. In a further embodiment the oligonucleotide is comprised of greater than 60% guanine monomers. In a further embodiment the oligonucleotide contains a region of 3 or more consecutive guanine monomers. In a further embodiment the oligonucleotide contains a region of 4 or more consecutive guanine monomers. In a further embodiment the oligonucleotide contains a region of 5 or more consecutive guanine monomers. In a further embodiment the oligonucleotide is SEQ ID NO:10.

The coupling reaction described herein is useful for initial coupling of a nucleoside phosphoramidite during the synthesis of an oligonucleotide to a universal support. Such universal supports are generally used in the art and can comprise a succinate-linker. Furthermore, the coupling reaction described herein is useful for coupling a nucleoside phosphoramidite during the synthesis of an oligonucleotide to a first nucleoside, wherein said first nucleoside may be free, or wherein said first nucleoside is immobilized on a support. Furthermore, the coupling reaction described herein is useful for coupling a nucleoside phosphoramidite during the synthesis of an oligonucleotide to an extending oligonucleotide.

Thus, in a further aspect, the invention relates to a method for coupling a nucleoside phosphoramidite during the synthesis of an oligonucleotide to a universal support, to a first nucleoside, or to an extending oligonucleotide, said method comprising the step of: (i) generating a coupling solution, wherein said coupling solution comprises: (a) at least one first solvent, wherein said at least one first solvent is a polar aprotic solvent, and wherein said at least one first solvent is not acetonitrile; (b) an activating reagent; and (c) said nucleoside phosphoramidite; wherein the concentration of said nucleoside phosphoramidite in said coupling solution is at least 0.03 M; and wherein preferably the concentration of said activating reagent in said coupling solution is at least 0.05 M; and (ii) contacting said coupling solution with said universal support, with said first nucleoside, or with said extending oligonucleotide. In a further aspect, the invention relates to a method for coupling a nucleoside phosphoramidite during the synthesis of an oligonucleotide to a first nucleoside or to an extending oligonucleotide, said method comprising the step of: (i) generating a coupling solution, wherein said coupling solution comprises: (a) at least one first solvent, wherein said at least one first solvent is a polar aprotic solvent, and wherein said at least one first solvent is not acetonitrile; (b) an activating reagent; and (c) said nucleoside phosphoramidite; wherein the concentration of said nucleoside phosphoramidite in said coupling solution is at least 0.03 M; and wherein preferably the concentration of said activating reagent in said coupling solution is at least 0.05 M; and (ii) contacting said coupling solution with said first nucleoside, or with said extending oligonucleotide.

In another embodiment said first solvent is not selected from the goup consisting of: (a) succinonitrile, (b) glutaronitrile, (c) adiponitrile, (d) pimelonitril, (e) valeronitril, (f) benzonitrile, (g) capronitrile. In a further embodiment said first solvent is not selected from the group consisting of: (a) dinitriles, (h) mononitriles, (c) glymes, (d) diglymes, (e) triglymes, (f) trimethylphosphates, (g) dichloromethane, (h) tetrahydrofuran, (i) dimethoxyethane, and (j) nitromethane. In a further preferred embodiment said polar aprotic solvent is a dipolar aprotic solvent.

In a further aspect, the invention relates to a method for coupling a nucleoside phosphoramidite during the synthesis of an oligonucleotide to a universal support, to a first nucleoside, or to an extending oligonucleotide, said method comprising the step of: (i) generating a coupling solution, wherein said coupling solution comprises: (a) at least one first solvent, wherein said at least one first solvent is a polar aprotic solvent; (b) an activating reagent; (c) said nucleoside phosphoramidite; and (d) a second solvent, wherein said second solvent is chemically different from any one of said at least one first solvent, and wherein preferably said second solvent is acetonitrile; wherein the concentration of said nucleoside phosphoramidite in said coupling solution is at least 0.03 M; and (ii) contacting said coupling solution with said universal support, with said first nucleoside, or with said extending oligonucleotide.

In a further embodiment said at least one first solvent is selected from the group consisting of: (a) sulfolane; (b) 1-methylpyrrolidin-2-one; (c) N,N-dimethylacetamide; (d) tetramethylurea; and (e) dimethylsulfoxide (DMSO); wherein preferably said at least one first solvent is selected from the group consisting of: (a) sulfolane; (b) 1-methylpyrrolidin-2-one; (c) N,N-dimethylacetamide; and (d) tetramethylurea. In another embodiment said at least one first solvent is sulfolane.

The method of any one of the preceding claims, wherein the concentration of said nucleoside phosphoramidite in said coupling solution is 0.03 to 0.3 M, 0.03 to 0.20 M, or 0.05 to 0.15 M.

In a further preferred embodiment the concentration of said activating reagent in said coupling solution is 0.05 to 0.90 M, 0.25 to 0.50 M, or 0.30 to 0.5 M. In a further embodiment said coupling solution comprises exactly one of said at least one first solvent.

In a further embodiment said coupling solution consists of: (a) exactly one of said at least one first solvent; (b) said activating reagent; and (c) said nucleoside phosphoramidite.

In a further embodiment said coupling solution further comprises a second solvent, wherein said second solvent is a weak basic solvent. In another embodiment said second solvent is acetonitrile.

It is apparent to the artisan, that said first and/or said second solvent can be provided in a water free form in order to facilitate the chemical reaction underlying the invention, in particular said coupling of said nucleoside phosphoramidite to said universal support, to said first nucleoside, or to said extending oligonucleotide.

In a further embodiment said coupling solution comprises: (a) exactly one of said at least one first solvent; (b) said activating reagent; (c) said nucleoside phosphoramidite; and (d) a second solvent, wherein preferably said second solvent is acetonitrile.

In a further embodiment the ratio (v/v) of said at least one first solvent to said second solvent is between 5:1 and 1:2, between 4:1 and 1:2, between 3:1 and 2:5, between 2:1 and 2:5, or between 2:1 and 1:1.

In a further embodiment the ratio (v/v) of said at least one first solvent to said second solvent is 5:1, 4:1, 3:1, 2:1, 1:1, or 1:2: wherein said ratio is about 1:1, or wherein most said ratio is 1:1.

In a further embodiment said first nucleoside and/or said extending oligonucleotide is immobilized on a support, wherein said support is selected from (a) polystyrene support; and (b) silica support, preferably a controlled pore glass (CPG) support.

In a further embodiment said support is a polystyrene support, wherein said polystyrene support is cross linked by divinylbenzene, wherein further said polystyrene support is characterized by functional hydroxyl groups; and wherein further said polystyrene support comprises an average particle size of about 90 μm.

In a further embodiment said oligonucleotide comprises at least 30%, at least 40%, at least 50%, at least 60%, at least 70%, and further at least 75% guanine monomers.

In a further embodiment said activating reagent is selected from the group consisting of: (a) 4,5-dicyanoimidazole (DCI); (b) 5-ethylihio-1H-tetrazole (ETT); (c) 5-benzylthio-1H-tetrazole (BTT); and (d) bis-trifluoromethyl)phenyl-1H-tetrazole (Activator 42). In one embodiment said activating reagent is 4,5-dicyanoimidazole (DCI).

In a further embodiment said oligonucleotide comprises a region of 3 or more, 4 or more, or 5 or more consecutive guanine monomers.

In a further embodiment said oligonucleotide comprises a first region of 3, 4, 5, 6, 7, 8, 9, 10, 11, 12, 13, 14, 15, 16, 17, 18, 19, or 20 consecutive guanine monomers.

In a further embodiment said oligonucleotide comprises a second region of 3, 4, 5, 6, 7, 8, 9, 10, 11, 12, 13, 14, 15, 16, 17, 18, 19, or 20 consecutive guanine monomers.

In a further embodiment said first region is located at the 3'-terminus of said oligonucleotide and/or wherein said second region is located at the 5'-terminus of said oligonucleotide.

In a further embodiment said oligonucleotide comprises 10 to 50, or alternatively 20 to 40, or alternatively 30 nucleotide monomers.

In a embodiment said oligonucleotide comprises a palindromic sequence; wherein said palindromic sequence is

```
                                          (SEQ ID NO: 2)
             GACGATCGTC.
```

In a further embodiment said palindromic sequence is flanked at its 5'-terminus by at least 4 and at most 20, preferably at most 10, guanosine entities; and/or wherein said palindromic sequence is flanked at its 3'-terminus by at least 6 and at most 20, preferably at most 10, guanosine entities.

In a further preferred embodiment said oligonucleotide comprises a nucleotide sequence selected from the group consisting of:

```
(a)
                                          (SEQ ID NO: 3)
    GGGGACGATC GTCGGGGGG;

(b)
                                          (SEQ ID NO: 4)
    GGGGGACGAT CGTCGGGGGG;

(c)
                                          (SEQ ID NO: 5)
    GGGGGGACGATCGTCGGGGGG;

(d)
                                          (SEQ ID NO: 6)
    GGGGGGGACG ATCGTCGGGGGG;

(e)
                                          (SEQ ID NO: 7)
    GGGGGGGGAC GATCGTCGGG GGGG;

(f)
                                          (SEQ ID NO: 8)
    GGGGGGGGGA CGATCGTCGG GGGGGG;

(g)
                                          (SEQ ID NO: 9)
    GGGGGGGGGG ACGATCGTCG GGGGOGGC;

(h)
                                          (SEQ ID NO: 10)
    GGGGGGGGGG GACGATCGTC GGGGGGGGGG;
    and (i)
                                          (SEQ 1D NO: 11)
    GGGGGGCG ACGACGAT CGTCGTCG GGGGGG.
```

In a further embodiment oligonucleotide is a deoxynucleotide, and wherein said deoxynucleotide consists exclusively of phosphodiester bound monomers.

In a further aspect, the invention relates to a method for producing an oligonucleotide, said method comprising any one of the methods described herein for coupling a nucleoside phosphoramidite during the synthesis of an oligonucleotide to an universal support, to a first nucleoside, or to an extending oligonucleotide.

In a further aspect, the invention relates to a method for producing an oligonucleotide, said method comprising (i) coupling a nucleoside phosphoramidite to a first nucleoside; wherein said coupling comprises any one of the methods described herein for coupling a nucleoside phosphoramidite during the synthesis of an oligonucleotide to a first nucleoside; (ii) generating an extending oligonucleotide by oxidizing the product of step (i); (iii) coupling a nucleoside phosphoramidite to the product of step (ii), typically after deprotection; wherein said coupling comprises any one of the methods described herein for coupling a nucleoside phosphoramidite during the synthesis of an oligonucleotide to an extending oligonucleotide; (iv) generating an extending oligonucleotide by oxidizing the product of step (iii); and (v) repeating steps (iii) and (iv) until said extending oligonucleotide comprises the sequence of said oligonucleotide.

In another embodiment said method further comprises the step of purifying said oligonucleotide under denaturing conditions, wherein said denaturing conditions are characterized by a pH of 10 to 14, preferably by a pH of 10 to 13, more preferably by a pH of about 12, most preferably by a pH of 12.

In a further embodiment said method further comprises the step of purifying said oligonucleotide at a pH of 10 to 14, preferably at a pH of 10 to 13, more preferably at a pH of about 12, most preferably at a pH of 12.

In a further embodiment, said purifying is performed by anion-exchange chromatography, wherein said anion exchange chromatography is performed using an anion-exchange matrix functionalized with quaternary amine groups, wherein further said anion-exchange matrix is composed of a material selected from polystyrene and polymethacrylate.

In a further embodiment said oligonucleotide is produced in a molar yield with respect to said first nucleoside of at least 20%, preferably at least 25%, more preferably at least 30%, still more preferably at least 35%, and most preferably at least 40%.

In a further embodiment the purity of said oligonucleotide is at least 75%, preferably at least 80%, more preferably at least 85%, still more preferably at least 90%, and most preferably at least 95%.

In a further aspect, the invention relates to the use of a coupling solution in a method for coupling a nucleoside phosphoramidite to a nucleoside or to an extending oligonucleotide, wherein said coupling solution comprises: (a) at least one first solvent, wherein said at least one first solvent is a polar aprotic solvent, and wherein said at least one first solvent is not acetonitrile; (b) an activating reagent; and (c) said nucleoside phosphoramidite; wherein the concentration of said nucleoside phosphoramidite in said coupling solution is at least 0.03 M; and wherein the concentration of said activating reagent in said coupling solution is at least 0.05 M. In another embodiment said method is further characterized by the features of any one of the methods described herein for coupling a nucleoside phosphoramidite during the synthesis of an oligonucleotide to a first nucleoside or to an extending oligonucleotide.

In a further aspect, the invention relates to a coupling solution for coupling a nucleoside phosphoramidite during the synthesis of an oligonucleotide to an universal support, to a first nucleoside, or to an extending oligonucleotide, wherein said coupling solution comprises: (a) at least one first solvent, wherein said at least one first solvent is a polar aprotic solvent, and wherein said at least one first solvent is not acetonitrile, and wherein said polar aprotic solvent is not adiponitrile; (b) an activating reagent; and (c) said nucleoside phosphoramidite; wherein the concentration of said nucleoside phosphoramidite in said coupling solution is at least 0.03 M; and wherein the concentration of said activating reagent in said coupling solution is at least 0.05 M. In another embodiment said method is further characterized by the features of any one of the methods disclosed herein. In another embodiment said coupling solution is characterized by any one of the features disclosed herein and in any possible combination.

A further embodiment is a coupling solution comprising (a) exactly one first solvent, wherein said exactly one first solvent is a polar aprotic solvent, and wherein said exactly one first solvent is selected from the group consisting of (i) sulfolane; (ii) 1-methylpyrrolidin-2-one; (iii) N,N-dimethylacetamide, (iv) tetramethylurea; and (v) dimethylsulfoxide (DMSO); (b) an activating reagent; (c) said nucleoside phosphoramidite; and (d) a second solvent, wherein said second solvent is acetonitrile; wherein the concentration of said nucleoside phosphoramidite in said coupling solution is at least 0.03 M; wherein the ratio (v/v) of said at exactly one first solvent to said second solvent is between 5:1 and 1:2, and wherein preferably said ratio is 1:1.

In a further aspect, the invention relates to an oligonucleotide obtainable by any one of the methods disclosed herein, in particular by any one of the methods for producing an oligonucleotide disclosed herein.

In a further embodiment said oligonucleotide comprises a nucleotide sequence selected from the group consisting of:

(a)
(SEQ ID NO: 3)
GGGGACGATC GTCGGGGGG;

(b)
(SEQ ID NO: 4)
GGGGGACGAT CGTCGGGGGG;

(c)
(SEQ ID NO: 5)
GGGGGGACGATCGTCGGGGGG;

(d)
(SEQ ID NO: 6)
GGGGGGGACG ATCGTCGGGGGG;

(e)
(SEQ ID NO: 7)
GGGGGGGGAC GATCGTCGGG GGGG;

(f)
(SEQ ID NO: 8)
GGGGGGGGGA CGATCGTCGG GGGGGG;

(g)
(SEQ ID NO: 9)
GGGGGGGGGG ACGATCGTCG GGGGOGGC;

(h)
(SEQ ID NO: 10)
GGGGGGGGGG GACGATCGTC GGGGGGGGGG;
and (i)
(SEQ 1D NO: 11)
GGGGGGCG ACGACGAT CGTCGTCG GGGGGG.

(a)
(SEQ ID NO: 3)
GGGGACGATC GTCGGGGGG;

(b)
(SEQ ID NO: 4)
GGGGGACGAT CGTCGGGGGG;

(c)
GGGGGGACGATCGTCGGGGGG; (SEQ ID NO: 5)

(d)
GGGGGGGACG ATCGTCGGGGGG; (SEQ ID NO: 6)

(e)
GGGGGGGGAC GATCGTCGGG GGGG; (SEQ ID NO: 7)

(f)
GGGGGGGGGA CGATCGTCGG GGGGGG; (SEQ ID NO: 8)

(g)
GGGGGGGGGG ACGATCGTCG GGGGOGGC; (SEQ ID NO: 9)

(h)
GGGGGGGGGG GACGATCGTC GGGGGGGGGG; (SEQ ID NO: 10)
and (i)
GGGGGGCG ACGACGAT CGTCGTCG GGGGGG. (SEQ 1D NO: 11)

wherein the purity of said oligonucleotide is at least 75%, preferably at least 80%, more preferably at least 85%, still more preferably at least 90%, and most preferably at least 95%. In a very preferred embodiment said oligonucleotide consists of SEQ ID NO:10.

The method disclosed herein is well suited for the large scale synthesis of oligonucleotides, in particular of G-rich oligonucleotides, such as, for example, poly G flanked unmethylated CpG containing oligonucleotides. Such compounds are used in pharmaceutical applications. For example, they are well known stimulators of the immune system. Thus, in a further aspect, the invention relates to the use of the oligonucleotide of the invention in the manufacture of a pharmaceutical and/or of a vaccine.

In a further aspect, the invention relates to a method for coupling a nucleoside phosphoramidite during the synthesis of an oligonucleotide to an universal support, to a first nucleoside, or to an extending oligonucleotide, said method comprising the step of: (i) generating a coupling solution, wherein said coupling solution comprises: (a) at least one first solvent, wherein said at least one first solvent is a polar aprotic solvent, and wherein said at least one first solvent is not acetonitrile; (b) an activating reagent; and (c) said nucleoside phosphoramidite; wherein the concentration of said nucleoside phosphoramidite in said coupling solution is at least 0.03 M; and wherein preferably the concentration of said activating reagent in said coupling solution is at least 0.05 M; and (ii) contacting said coupling solution with said universal support, with said first nucleoside, or with said extending oligonucleotide. In a preferred embodiment, said first solvent is not adiponitril.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The following examples further illustrate the invention but, of course, should not be construed as in any way limiting its scope.

Example 1

This example describes the solvents tested for compatibility with oligomer synthesis. The following solvents were tested.

1-Methylpyrrolidin-2-one (NMP)—MW 99.13; density 1.032 g/ml; viscosity 1.67 cP; dipole moment 4.09 D. Peptide synthesis grade was obtained from Fluka (catalog no. 69116; lot & filling code 1059178, 21504055). Purity by GC is ≤99.5% and water content is ≤0.02%.

N,N-Dimethylacetamide (DMA)—MW 87,12; density 0.942 g/ml; viscosity 1.02 cP at 20° C.; dipole moment 3.79 D. puriss. grade was obtained from Fluka (catalog no. 38840; lot & filling code 454936/1, 40504059). Purity by GC is ≥99.5%.

Tetramethylurea (TMU)—MW 116.16; density 0.968 g/ml. BioChemika grade was obtained from Fluka (catalog no. 87849; lot & filling code 1063403, 30205010). Purity by GC is ≥99.5%. This material was dried for 48 h over 4 Angstrom molecular sieves prior to use.

Dimethylsulfoxide (DMSO)—MW 78.13; density 1.100 g/ml; viscosity 1.996 cP at 20° C.: dipole moment 3.96 D. Puriss. absolute over molecular sieves was obtained from Fluka (catalog no. 41647, lot & filling code 1073729, 22404456). Purity by GC is ≥99.5% and water content is ≤0.005%

Sulfolane—MW 120.17; density 1.293 g/ml; viscosity 10.30 cP at 30° C.; dipole moment 4.8 D Puriss. grade was obtained from Fluka (catalog no. 86148, lot & filling code 1181025, 42306336). Purity by GC is ≥99.5%. This material was first liquefied in an oven at 35° C. then dried for 48 h over 4 Angstrom molecular sieves prior to use.

1,1,1,3,3,3-Hexafluoro-2-propanol (HFIP)—MW 168.04; density 1.596 g/ml. UV spectroscopic grade was obtained from Apollo Scientific (catalog no. PC 0877, lot no. BNO HFIP-05-14). HELP is a polar hydroxylic solvent frequently used to solubilize peptides, and was therefore included as a control.

Example 2

The following example demonstrates the solubility of monomers and 5-benzylthiotetrazole (BTT) in a 1:1 by volume mix of acetonitrile and a solvent from Example 1.

The BTT (MW 192.2, water content ≤75 ppm) was supplied by emp Biotech GmbH (catalog no. NC-0101-1K, charge/lot no. 050904). The dT (MW 744.83), dG$^{ibu}$ (MW 839.92), dA$^{bz}$ (MW 857.93), dC$^{bz}$ (MW 833.93) monomers were supplied by Proligo. The acetonitrile (MeCN) has a viscosity of 0.345 cP at 25° C. and a dipole moment of 3.92 D.

74.5 mg (100 μmol) of dT monomer was weighed out into each of 7 screw-topped 10 ml vials. 84 mg (100 μmol) of dG$^{ibu}$ monomer was weighed out into each of 7 screw-topped 10 ml vials. 86 mg (100 μmol) of dA$^{bz}$ monomer was weighed out into each of 7 screw-topped 10 ml vials. 83 mg (100 μmol) of dC$^{bz}$ monomer was weighed out into each of 7 screw-topped 10 ml vials. 228 mg (1.2 mmol) of BTT was weighed out into each of 7 screw-topped 10 ml vials.

Six different solvent mixes were prepared by mixing 10 ml of dry acetonitrile with 10 ml of one of the 6 different solvents listed above in separate dry bottles under argon.

To each separate vial of T monomer was added 1 ml of one of the 6 different solvent mixes or pure acetonitrile. The vials were quickly closed and agitated gently. This was repeated with the vials of dG, dA and dC monomers. All monomers dissolved fairly rapidly (within 10 min, in the case of MeCN/sulfolane dissolution was somewhat slower) in all the 7 solvent mixes at a concentration of 0.1 M as is required for use on standard synthesizers. Clear colorless solutions were obtained.

To each separate vial of BTT was added 4 ml of one of the 6 solvent mixes. In all cases except for HFIP/MeCN dissolution was practically instantaneous at 0.3M, a typical standard concentration for DNA and RNA synthesis. BTT was added to pure acetonitrile, and the dissolution was not as fast as the dissolution in the 6 solvents from Example 1. Gentle warming was required to achieve rapid dissolution in pure acetonitrile.

All 4 standard protected DNA monomers are readily soluble at 0.1 M in 1:1 mixes between acetonitrile and NMP, DMA, TMU, DMSO and sulfolane. BTT is soluble in all 5 mixes at 0.3 M.

Example 3

The following example demonstrates the monomer stability in the solvent solutions after 48 hours. In order to check the stability of the monomers in the various solvent mixes, silica gel tlc analyses were performed on a 1 μl aliquot of each of the 28 monomer solutions after standing for 48 h at room temperature. Clearly any appreciable instability shown means that that particular solvent combination is not useful for DNA synthesis on a synthesizer. For this purpose the eluent chosen was ethyl acetate/1,2-dichloroethane (1:2 v/v) containing 3% triethylamine. All monomer solutions except those in MeCN/HFIP (these were all pale yellow, probably due to detritylation and degradation) were still colorless. Silica gel, with fluorescent indicator 254 nm, on aluminium cards for tlc was from Mica (catalog no. 60778, lot no. 503 066).

The following spots were observed for the various monomers in the 6 relevant solvent mixes. Solvent mix MeCN/HFIP ted to a total degradation of all 4 monomers as was largely expected, with multiple spots on tlc with $R_f$s from 0 to 0.21. The results are listed in Table 1.

TABLE 1

Silica gel tlc analysis results.

| solvent | $R_f$-dA | $R_f$-dG | $R_f$-dC | $R_f$-dT |
|---|---|---|---|---|
| NMP | 0.48, 0.43 | 0.41 | 0.41 | 0.47, 0.42 |
| DMA | 0.47, 0.43 | 0.40 | 0.43 | 0.47, 0.43 |
| TMU | 0.49, 0.46 | 0.46 | 0.46 | 0.52, 0.49 |
| DMSO | 0.39, 0.34 | 0.35, 0.30 | 0.39, 0.34 | 0.47, 0.41 |
| Sulfolane | 0.46 | 0.40, 0.23 | 0.42 | 0.49 |

In the case of TMU the tlc spots had slightly increased $R_f$s relative to the values in NMP, and DMA. In DMSO $R_f$s were somewhat reduced. In most cases both diastereoisomers were observed. In the cases of NMP, DMA, TMU and DMSO very faint impurity spots could also be observed. In the case of sulfolane a faint impurity spot of $R_f$0.27 was observed with the dC$^{bz}$ monomer.

All 4 standard protected DNA monomers show very little/no degradation after 48 h in solution at room temperature. All 5 mixes seem suitable for attempting syntheses of oligo-dG containing sequences on small scale.

Example 4

The following example demonstrates the utility of the solvents in Example 1 when used in the coupling step during synthesis of a g-rich oligonucleotide on an ABI 394 DNA/RNA synthesizer (Applied Biosystems). The following guanine-rich oligonucleotide was chosen for synthesis.

SEQ ID NO: 1
d[GGGGGGGGGG]

The calculated delivery factors to allow for the change in viscosity relative to pure acetonitrile are given in Table 2.

TABLE 2

Flow rate factors for alternative solvents.

| Solvent | Factor |
|---|---|
| MeCN | 1 |
| NMP/MeCN | 1.74 |
| DMA/MeCN | 1.33 |
| TMU/MeCN | 1.42 |
| DMSO/MeCN | 2.61 |
| Sulfolane/MeCN | 2.41 |

The cycle parameters on the ABI 394 synthesizer were adjusted. For 1 μmole scale DNA syntheses cycle no. 20, whose relevant monomer and monomer+tet delivery times in seconds are illustrated in the table below, was used. The corrected delivery times for the 5 different 1:1 solvent mixes are also shown in Table 3.

TABLE 3

Adjustment of cycle parameters for ABI 394 synthesizer-

| Step | Function | MeCN | NMP | DMA | TMU | DMSO | Sulfolane |
|---|---|---|---|---|---|---|---|
| 9 | tet to waste | 1.7 | 3.0 | 2.3 | 2.4 | 4.4 | 4.1 |
| 10 | B + tet to col | 2.5 | 4.4 | 3.3 | 3.6 | 6.5 | 6.0 |
| 11 | tet to col | 1.0 | 1.7 | 1.3 | 1.4 | 2.6 | 2.4 |
| 12 | B + tet to col | 2.5 | 4.4 | 3.3 | 3.6 | 6.5 | 6.0 |

The following synthesis parameters on the ABI 394-08 were used. Trityl-off syntheses of $(dG)_{10}$ were performed on a 1 µmol scale on both controlled pore glass (CPG) and polystyrene (PS) supports using pure acetonitrile as solvent for the condensation step as well as each of the 1:1 mixes of NMP, DMA, TMU, DMSO and sulfolane with acetonitrile. DNA synthesis cycle 20 was used, comprising the following five steps: (I) detritylation with 5% DCA in 1,2-diehloroethane (DCE) for 75 sec; (2) coupling for 5 min with 0.5M DCI plus 0.1 M dG monomer in the appropriate solvent mixture; (3) capping with tae anhydride/McCN for 1 min; (4) oxidation for 1 min with 50 mM $I_2$ in pyridine/water (9:1 v/v); and (5) capping for 5 sec. The delivery times for "tet to waste", "B+tet to column" and "tet to column" were adjusted according to the table above for the various solvent mixtures.

CPG dG(tac) 500A support was supplied by SAFC Proligo (product no. G302001, bulk no. 5452, lot no. 223460) and had a loading of 35 µmol/g. Thus, 28.6 mg is equivalent to 1 µmol. $dG^{ibu}$ SOS polystyrene support loaded at 79 µmol/g was obtained from GE Healthcare, order no. 17-5252-82, lot no. 1503095, bottle 12. 12.7 mg is equivalent to 1 µmol. 4,5-Dicyanoimidazole (DCI) was obtained from SAFC Proligo (product no. M700100, lot. no. 231206). MW is 118.1. A 0.5 M solution is 2.95 g dry DCI in 50 ml of acetonitrile or other solvent. $dG^{ibo}$ monomer was from SAFC Proligo (product no. G111010-01, lot no. 230394, bottle 17). MW is 839.92. 420 mg are needed for 5 ml of 0.1 M solution. Extra dry 1,2-dichloroethane, 99.8% by GC, was from Acros Organics (product code 32684 0010, lot no. A0208016). 50 mM iodine solution for oxidation was from Biosolve (cat. no. 15072402, batch no. 455001). Dichloroacetic acid (DCA) was from Fluka, catalogue no. 35810, lot no. S36318 12306B12. Cap B ACN was from SAFC Proligo, cat. no. LB50250, batch no. 16673. Cap 2 ACN was from SAFC Proligo, cat. no. LR50250, batch no. 16950.

420 mg of $dG^{ibo}$ monomer was placed into each of the six separate ABI 10 ml amidite bottles and dried in vacuo overnight over $P_7O_5$ and KOH pellets. The vacuum was released with argon and each monomer was dissolved in one of the solvent mixes. 2 95 g aliquots of DCI were weighed out into six 250 ml ABI bottles and dried in vacuo. Each portion of DCI was dissolved in one of the 6 different solvents (5 mixes plus 1 pure acetonitrile).

Six ABI snap columns were filled with 28.6 mg dG(tac)-CPG and 6 columns were filled with 12.7 mg $dG^{ibo}$ 80S polystyrene support. Prior to use in solid-phase synthesis the PS support was swollen for 10 min in acetonitrile.

Prior to each synthesis start an ABI begin protocol was used, to ensure that all delivery lines were filled with fresh reagent. The Trityl colors were consistent with successful coupling.

All 12 supports were deprotected in 3 ml of 40 wt. % methylamine in water (Aldrich, cat. no. 42,646-6, lot no. S23322-405) for 2.5 h at 65° C. in well sealed screw-top glass vials. After cooling, the supernatants were filtered into Falcon tubes and the supports were each washed with 3 ml of 20% aqueous ethanol. The washings were filtered and combined with the corresponding filtrates. The samples were then concentrated in vacuo in a Speedvac to about 2 ml. Each sample was diluted with pure water to a total volume of 5 ml.

In order to determine the total ODs at 260 nm in each sample, a 50 µl aliquot of each was diluted to 1 ml with 1 M Tris HCl buffer pH 7.6 (Fluka BioChemika Ultra grade for molecular biology, cat no. 93314, lot & filling code 1188960 54605275). Measured $A_{260m}$ in a 1 cm pathlength disposable cuvette (Plastibrand, 1.5 ml semi-micro, cat. no. 7591 50) for each of the solutions. The corrected crude ODs/µmol for each synthesis are shown in Table 4.

TABLE 4

ODs/µmol for solvent syntheses.

| Coupling Solvent | ODs/µmol on CPG | ODs/µmol on PS |
|---|---|---|
| MeCN | 93.3 | 81.0 |
| DMSO/MeCN | 56.1 | 53.8 |
| DMA/MeCN | 77.1 | 78.0 |
| Sulfolane/MeCN | 90.3 | 65.1 |
| NMP/MeCN | 64.2 | 73.4 |
| TMU/MeCN | 62.1 | 75.0 |

Anion-exchange HPLC analyses were then performed on all 12 crude syntheses. 0.5 ml of each crude synthesis in 5 ml water was mixed with 0.5 ml of HPLC buffer A (50 mM NaCl 10 mM NaOH and 0.2 mM EDTA in water). The 14×1 ml samples were placed in 1.5 ml short thread autosampler vials (VWR International, cat./art. no. 548.0177, batch no. 19310/20060763) which were loaded into the tray of an A-900 autosampler (GE Healthcare) connected to an Akta Explorer 10 HPLC system (GE Healthcare). 50 µl samples were injected from the vials and separated on a DNAPac-100 column (Dionex) at 50° C. (Thermasphere column heater, Phenomenex) using a gradient from 0 to 40% B during 25 min with a flow rate of 1 ml/min and uv detection at 260, 280 and 295 nm. B buffer was 2.5 M NaCl, 10 mM NaOH and 0.2 mM EDTA in water. The % full length product for each solvent mix and each support are given in Table 5.

TABLE 5

% Full-length product for solvent syntheses.

| Coupling Solvent | % Full-length on CPG | % Full-length on PS |
|---|---|---|
| MeCN | 82.24 | 80.24 |
| DMSO/MeCN | 51.93 | 34.42 |
| DMA/MeCN | 80.84 | 85.03 |
| Sulfolane/MeCN | 85.61 | 76.13 |
| NMP/MeCN | 80.75 | 78.49 |
| TMU/MeCN | 73.00 | 80.02 |

For MeCN on CPG, the HPLC traces showed 12% impurities in front of the product peak and 3.5% n+ material. The peak height was 863 rnAU. Result file Autosampler DNAPac028. For PS, the traces showed 12% impurities in front of the product peak and 3.3% n+ material. The peak height was 817 mAU. Result file Autosampler DNAPac008.

For DMSO/MeCN on CPG, the HPLC traces showed largely incomplete couplings with a product peak of 347 mAU. The PS product peak height was 215 mAU. Result file Autosamplcr DNAPac009.

For DMA/MeCN on CPG, the HPLC traces showed that there were only small amounts of incomplete coupling.

There was 8.1% impurities in front of main peak all with reasonably uniform intensities, and 5.1% n+ material. The product peak height was 725 mAU. Result file Autosampler DNAPar003. For PS, there was only 10.4% impurities in front of product peak, and only 0.4% n+ material. The product peak height was 805 mAU. Result file Autosampler DNAPac010.

For sulfolane/MeCN on CPG, the HPLC traces showed only very small failure peaks (incomplete coupling) and 7.2% impurities in front of the product peak with 4.6% n+ material. The product peak height was 867 mAU. Result file Autosampler DNAPac-004. For PS, there was only 0.8% n+ material. Product peak height 683 mAU. Result file Autosampler DNAPac011.

For NMP/MeCN on CPG, the HPLC traces showed all failures of approx. equal size with 6.3% failures in front of main peak and about 4.8% n+ material. The product peak height was 639 mAU. Result file Autosampler DNAPac005. For PS, there was a few more pronounced failures, but only 0.7% n+ material. The product peek height was 748 mAU. Result file Autosampler DNAPac012.

For TMU/MeCN on CG, the HPLC traces showed 7% failures in front of the product peak and about 7.5% total n+ material. The product peak height was 551 mAU. Result file Autosampler DNAPac007. For PS, there was about 11.8% failures in front of product peak, which was very similar to the results obtained using pure MeCN. Total n+ material was only 2.7%. The product peak height was 735 mAU. Result file Autosampler DNA Pac014.

Example 5

The following example demonstrates a 1 μmol scale synthesis of

SEQ ID NO: 10
d(GGGGGGGGGG ACGATCGTCGGGOGGGGGG)

on CPG, GE polystyrene and NittoPhase supports using pure acetonitrile as solvent for the condensation step as well as each of the 1:1 mixes of DMA, sulfolane, NMP and TMU with acetonitrile.

The Example 4 cycle and parameters were used with the following exceptions. The synthesis included dA$^{bz}$ monomer from SAFC Proligo (product no. A111010-01, lot no. 228992; MW is 854.93; 215 mg are needed for 2.5 ml of 0.1 M solution); dC$^{bac}$ monomer from SAFC Proligo (product no. C111020-01, lot no. 229934; MW is 920.04; 299 mg are needed for 3.25 ml of 0.1 M solution); and dT monomer from SAFC Proligo (product no. T111010-01, lot no. 231062; MW is 744.81; 186 mg are needed for 2.5 ml of 0.1 M solution). 840 mg of dG$^{iba}$ monomer were placed into each of the 5 separate ABI 10 ml amidite bottles and dried in vacuo overnight over P$_2$O$_5$ and KOH pellets. Released vacuum with argon and dissolved each monomer in the appropriate volume of one of the solvent mixes. 5.9 g aliquots of DCI were weighed out into each of 5 180 ml AIR bottles and dried in vacuo. Each portion of DCI was dissolved in one of the 5 different solvents (4 mixes plus 1 pure acetonitrile).

The 5 ABI snap columns were filled with approx. 28.6 mg dG(tac)-CPG, 5 columns were filled with approx. 12.7 mg dG$^{ibu}$ 80S polystyrene support and 5 columns were filled with approx. 11.9 mg of NittoPhase dG$^{ibo}$ support. The exact amounts are listed in Table 6. Prior to use in solid-phase synthesis, the PS supports were swollen for 10 min in acetonitrile.

TABLE 6

Cartridge specifications for ABI 394-08 syntheses

| dG(tac)-CPG (Proligo, bulk 5452, lot 223460, 35 μmol/g) cartridges | | | |
|---|---|---|---|
| G1 | 28.8 (mg) | 1.007 (μmol) | MeCN |
| G2 | 28.7 | 1.003 | DMA/MeCN |
| G3 | 29.4 | 1.028 | Sulfolane/MeCN |
| G4 | 29.4 | 1.028 | NMP/MeCN |
| G5 | 30.2 | 1.056 | TMU/MeCN |
| dG$^{ibu}$ 80S (GE Healthcare, lot no. 1503095, 79 μmol/g) cartridges | | | |
| P1 | 13.3 | 1.047 | MeCN |
| P2 | 13.6 | 1.071 | DMA/MeCN |
| P3 | 13.4 | 1.055 | Sulfolane/MeCN |
| P4 | 13.5 | 1.063 | NMP/MeCN |
| P5 | 13.2 | 1.039 | TMU/MeCN |
| Nittophase TOS dGibu (Nitto Denko, 84 μmol/g) cartridges | | | |
| N1 | 13.2 | 1.109 | MeCN |
| N2 | 13.4 | 1.126 | DMA/MeCN |
| N3 | 13.4 | 1.126 | Sulfolane/MeCN |
| N4 | 12.4 | 1.042 | NMP/MeCN |
| N5 | 13.3 | 1.118 | TMU/MeCN |

Prior to each synthesis start an ABI begin protocol was used, to ensure that all delivery lines were filled with fresh reagent. At the end of the syntheses the cartridges were blown dry with an argon stream.

The cartridges were opened carefully and the supports were transferred into 4 ml screw-top glass vials and deprotected with 3 ml of 40 wt. % methylamine in water (Aldrich, cat. no. 42,646-6, lot no. S23322-405) for 2 h at 65° C. After cooling, the supernatants were filtered into Falcon tubes and the supports were each washed with 2×3 ml of 20% aqueous ethanol. The washings were filtered and combined with the corresponding filtrates. The sample volumes were adjusted to 10 ml and a 35 μl aliquot of each was removed for analysis by anion-exchange HPLC (525 μl aliquots were removed for samples G4, P4, N4, G5, P5 and N5 and each mixed with 475 μl water and the solutions were placed in autosampler vials which were then run on the autosampler coupled to an Akta Explorer 10 HPLC system). HPLC analyses were performed on an analytical DNAPac PA-100 column, 4×250 mm (Dionex, product no. 043010, lot no. 005-21-017 and serial no. 005402). A linear gradient was run from 0-50% B during 40 min with a flow rate of 1 ml/min and the column effluent was monitored by UV at 260, 280 and 295 nm. Buffer A was 50 mM NaCl and 10 mM NaOH in water and buffer B was 2 5 M NaCl and 10 mM NaOH in water. The % full length product obtained by integrating all the peaks in each run is shown in Table 7.

The solutions were then concentrated to dryness in vacuo in a Speedvac. Each sample was diluted with pure water to a total volume of 10 ml. In order to determine the total ODs at 260 nm in each sample, a 30 μl aliquot of each was diluted to 1 ml with 1 M Tris HCl buffer pH 7.6 (Fluka BioChemika Ultra grade for molecular biology, cat no. 93314, lot & filling code 1188960 54605275). Measured A$_{260nm}$ in a 1 cm pathlength disposable cuvette (Plastibrand, 1.5 ml semimicro, cat. no. 7591 50) for each of the solutions. The corrected crude ODs/μmol for each synthesis is shown in Table 7.

TABLE 7

Results of 1 µmol syntheses for Example 5.

| Coupling Solvent | | ODs/µmol | % FLP by anion exchange HPLC |
|---|---|---|---|
| MeCN | G1 | 202.6 | 78.93 |
|  | P1 | 163.3 | 72.68 |
|  | N1 | 202.3 | 84.78 |
| DMA/MeCN | G2 | 135.6 | 63.78 |
|  | P2 | 151.0 | 65.96 |
|  | N2 | 194.8 | 77.09 |
| Sulfolane/MeCN | G3 | 162.7 | 76.14 |
|  | P3 | 125.8 | 55.66 |
|  | N3 | 191.2 | 87.53 |
| NMP/MeCN | G4 | 132.1 | 62.55 |
|  | P4 | 142.9 | 51.51 |
|  | N4 | 178.2 | 75.36 |
| TMU/MeCN | G5 | 74.6 | 48.10 |
|  | P5 | 148.2 | 64.32 |
|  | N5 | 128.3 | 68.19 |

Example 6

The following example demonstrates a large-scale synthesis of guanine-rich oligonucleotide G10 (SEQ ID NO: 10). G10 was synthesized on an OligoPilot 100 using an OPII column packed with NittoPhase support loaded at 120 µmol/g with dG$^{ibu}$ and using DCI as a condensing agent in a 1:1 v/v mixture of acetonitrile/sulfolane as solvent for the condensation step.

Synthesis. A trityl-off synthesis was performed on a 2.4 mmol scale on the Akta OligoPilot 100 synthesizer using 20 g of NittoPhase™ dG$^{ibu}$ support (lot no. 195136) loaded at 120 µmol/g and packed in an OPII column (6 cm internal diameter, GE Healthcare code no. 18-1107-60) adjusted to a column volume of 133 mL (see below). The monomer concentrations (4-fold excess) used were 0.27 M in acetonitrile/sulfolane (1:1 v/v), and 0.5 M DCI in acetonitrile/sulfolane (1:1 v/v) was used as coupling agent with a 10 minute coupling time. The monomer concentrations were calculated as follows: The volume of the recycle loop is 5 mL, the column volume used was 120 mL (this is the volume of the support when swollen in toluene, based on 6.0 mL/g), and the open volume available in the packed column is 0.7×120=84 mL, thus giving a total open volume of 89 mL. This represents the maximum volume of activator plus amidite solution that can be added for a coupling. Since the ratio of activator solution to monomer solution was set to 60:40 v/v for the coupling mixture, then the volume of monomer solution to be added is 35.6 mL and this contains 9.6 mmol (4-fold excess) of monomer; hence the monomer concentration is 0.27 M. The volume of activator solution added for the coupling is 53.4 mL, which corresponds to 26.7 mmol, giving a ratio of DCI:monomer of 2.78:1. The support was swollen and packed in toluene and then washed with acetonitrile prior to starting the synthesis.

Deprotection. At the end of the synthesis the support-bound oligonucleotide was treated with 20% diethylamine (DEA) in dry acetonitrile to remove the cyanoethyl protecting groups Crude yield and Crude purity: Crude yield was found 187.8 A$_{260}$ units/µmol and the crude purity was determined 70.25% by HPLC.

Purification. The next step was the preparative anion-exchange HPLC purification of crude G10 in 4 runs on a Waters AP-5, 50×200 mm column (part no. WAT023322), packed to a bed height of 18.9 cm with TSK·GEL SuperQ-5PW 20 µm, and eluted at 50 mL/min with a linear gradient from 10-55% B during 82.5 min using the prep. HPLC buffer compositions identified above.

The pH of the crude G10 solution was adjusted to 12 just prior to loading and the sample was filtered once more. 40 mL fractions were collected and analyzed by analytical anion-exchange HPLC as above. Only fractions with an analytical purity, as measured by anion-exchange HPLC, in excess of 85% were pooled. All peak fractions were immediately neutralized with acetic acid to pH 6-8 prior to analysis.

Desalting. The combined fractions of pure G10 from above (total volume 2700 mL) were concentrated to 300 mL on a Pall Centramate 500S benchiop tangential flow filtration (TFF) system (part no. CM500SE, commission no. C500S-2017)) fitted with a single 1 kDa Centramate Omega, medium screen cassette (Pall, part no. OS001C12, serial no. 36324055R) with a surface area of 0.093 m$^2$. Thirteen continuous diafiltration cycles against pure water were then performed to remove the salt and buffers. The retentate was further concentrated to a volume of 200 mL.

Example 7

The overall process yield of the synthesis described in Example 6 was determined by calculating the molar amount of starting material such that the weight of support used was multiplied with the loading (e.g 20 g×120 µmol/g=2.4 mmol). 100% yield would be the same molar amount of product, considering the molar mass of the product (i.e. 9612 mmol/mg for SEQ ID NO: 10). The yield is the relative amount actually produced as quantified by UV spectroscopy using a product specific extinction coefficient (for SEQ ID NO:10 1 AU260-340=27.8 µg, at a path length of 1 cm). The overall process yield of the synthesis described in Example 6 was found to be 31.4%.

The purity of the resulting oligonucleotide is determined by HPLC analysis, carried out such that 40 µl of a 5 to 100 µM solution of product is injected onto a DNAPac PA-100 column at an oven temperature of 25° C. The column was equilibrated with 75% Buffer A (20 mM NaOH) and 25% Buffer B (20 mM NaOH, 1.5 M NaCL, 40% Methanol). A flow rate of 0.75 ml/min was applied. The detection wavelength was 215 nm. One minute after injection, a gradient was started which increased the percentage of buffer B to 40% within 4 minutes, then, the percentage of buffer B was increased to 55% within the next 35 minutes. Then, the percentage of buffer B was increased to 100% within one minute and kept such for 3 minutes, then the percentage of buffer B was lowered to 25% within 3.9 minutes. The purity is the relative peak area under the main peak of the total peak area over the entire chromatogram. Integration limits were set such that valley to valley integration was performed. The purity of the product of the synthesis described in Example 6 was found to be 87.75%.

Example 8

Synthesis of the oligonucleotide G10 (SEQ ID NO:10) is performed essentially as described in Example 5. The following mixtures of polar aprotic solvents with MeCN are tested and compared to MeCN alone: 1.) DMA/MeCN, 2.) Sulfolane/MeCN, 3.) NMP/MeCN, and 4.) TMU/MeCN. The experiment is repeated 6 times in duplicate, wherein in each repetition the ration (v/v) of said solvent to MeCN is varied from 5:1, 4:1, 3:1, 2:1, 1:1, to 1:2. Yield and purity of the product are determined as described and compared.

The invention claimed is:

1. A method for coupling a nucleoside phosphoramidite during the synthesis of an oligonucleotide to a universal support, to a first nucleoside, or to an extending oligonucleotide, wherein said oligonucleotide comprises at least 30% guanine monomers, and wherein said oligonucleotide comprises a first region of 3 or more consecutive guanine monomers and a second region of 3 or more consecutive guanine monomers, said method comprising:

(i) generating a coupling solution, wherein said coupling solution comprises:
   (a) at least one first solvent, wherein said at least one first solvent is a polar aprotic solvent, and wherein said at least one first solvent is not acetonitrile, wherein said coupling solution further comprises a second solvent, wherein said second solvent is acetonitrile, and wherein the ratio (v/v) of said at least one first solvent to said second solvent is between 3:1 and 2:5;
   (b) an activating reagent; and
   (c) said nucleoside phosphoramidite;
   wherein the concentration of said nucleoside phosphoramidite in said coupling solution is at least 0.03 M; and (ii) contacting said coupling solution with said universal support, with said first nucleoside, or with said extending oligonucleotide.

2. The method of claim 1, wherein said at least one first solvent is selected from the group consisting of:
(a) sulfolane;
(b) 1-methylpyrrolidin-2-one;
(c) N,N-dimethylacetamide;
(d) tetramethylurea; and
(e) dimethylsulfoxide (DMSO).

3. The method of claim 1, wherein the concentration of said nucleoside phosphoramidite in said coupling solution is 0.03 to 0.30 M.

4. The method of claim 1, wherein the ratio (v/v) of said at least one first solvent to said second solvent is 1:1.

5. The method of claim 1, wherein said first nucleoside and/or said extending oligonucleotide is immobilized on a support.

6. The method of claim 1, wherein said support is a polystyrene support, wherein said polystyrene support is cross linked by divinylbenzene.

7. The method of claim 1, wherein said oligonucleotide comprises a first region of 4, 5, 6, 7, 8, 9, 10, 11, 12, 13, 14, 15, 16, 17, 18, 19, or 20 consecutive guanine monomers.

8. The method of claim 7, wherein said oligonucleotide comprises a second region of 4, 5, 6, 7, 8, 9, 10, 11, 12, 13, 14, 15, 16, 17, 18, 19, or 20 consecutive guanine monomers.

9. The method of claim 8, wherein said first region is located at the 3'-terminus of said oligonucleotide and/or wherein said second region is located at the 5'-terminus of said oligonucleotide.

10. The method of claim 1, wherein said oligonucleotide comprises 10 to 50 nucleotide monomers.

11. The method of claim 1, wherein said oligonucleotide comprises a nucleotide sequence selected from the group consisting of:

(a)
(SEQ ID NO: 3)
GGGGACGATCGTCGGGGGG;

(b)
(SEQ ID NO: 4)
GGGGGACGATCGTCGGGGGG;

(c)
(SEQ ID NO: 5)
GGGGGGACGATCGTCGGGGGG;

(d)
(SEQ ID NO: 6)
GGGGGGGACGATCGTCGGGGGG;

(e)
(SEQ ID NO: 7)
GGGGGGGGACGATCGTCGGGGGGG;

(f)
(SEQ ID NO: 8)
GGGGGGGGGACGATCGTCGGGGGGGG;

(g)
(SEQ ID NO: 9)
GGGGGGGGGGACGATCGTCGGGGGGGGG;

(h)
(SEQ ID NO: 10)
GGGGGGGGGGGACGATCGTCGGGGGGGGGG;
and (i)
(SEQ ID NO: 11)
GGGGGGCGACGACGATCGTCGTCGGGGGGG.

12. The method of claim 1, wherein said nucleoside phosphoramidite is coupled to an extending oligonuclotide.

13. A method for producing an oligonucleotide, wherein said oligonucleotide comprises at least 30% guanine monomers, and wherein said oligonucleotide comprises a first region of 3 or more consecutive guanine monomers and a second region of 3 or more consecutive guanine monomers, said method comprising
(i) coupling a nucleoside phosphoramidite to a first nucleoside; wherein said coupling comprises the method of claim 1;
(ii) generating an extending oligonucleotide by oxidizing the product of step (i);
(iii) coupling a nucleoside phosphoramidite to the product of step (ii) after deprotection; wherein said coupling comprises the method of claim 1;
(iv) generating an extending oligonucleotide by oxidizing the product of step (iii); and
(v) repeating steps (iii) and (iv) until said extending oligonucleotide comprises the sequence of said oligonucleotide.

14. The method of claim 13, wherein said method further comprises the step of purifying said oligonucleotide under denaturing conditions, wherein said denaturing conditions are characterized by a pH of 10 to 14.

15. The method of claim 14, wherein said purifying is performed by anion-exchange chromatography.

16. The method of claim 14, wherein said oligonucleotide comprises a nucleotide sequence selected from the group consisting of:

(a)
(SEQ ID NO: 3)
GGGGACGATCGTCGGGGGG;

(b)
(SEQ ID NO: 4)
GGGGGACGATCGTCGGGGGG;

(c)
(SEQ ID NO: 5)
GGGGGGACGATCGTCGGGGGG;

(d)
(SEQ ID NO: 6)
GGGGGGGACGATCGTCGGGGGG;

(e)
(SEQ ID NO: 7)
GGGGGGGGACGATCGTCGGGGGGG;

(f)
(SEQ ID NO: 8)
GGGGGGGGGACGATCGTCGGGGGGGG;

(g)
(SEQ ID NO: 9)
GGGGGGGGGGACGATCGTCGGGGGGGGG;

(h)
(SEQ ID NO: 10)
GGGGGGGGGGGACGATCGTCGGGGGGGGGG;
and (i)
(SEQ ID NO: 11)
GGGGGGCGACGACGATCGTCGTCGGGGGGG.

17. The method of claim 1, wherein said coupling solution comprises exactly one of said at least one first solvent.

18. The method of claim 1, wherein the ratio (v/v) of said at least one first solvent to said second solvent is between 2:1 and 2:5.

19. The method of claim 1, wherein the ratio (v/v) of said at least one first solvent to said second solvent is between 2:1 and 1:1.

20. The method of claim 1, wherein said activating reagent is selected from the group consisting of:
(a) 4,5-dicyanoimidazole (DCI);
(b) 5-ethylthio-1H-tetrazole (ETT);
(c) 5-benzylthio-1H-tetrazole (BTT); and
(d) 5-(3.5-bis-trifluoromethyl)phenyl-1H-tetrazole (Activator 42).

* * * * *

SEQUENCE LISTING

<160> NUMBER OF SEQ ID NOS: 11

<210> SEQ ID NO 1
<211> LENGTH: 10
<212> TYPE: DNA
<213> ORGANISM: Artificial sequence
<220> FEATURE:
<223> OTHER INFORMATION: Synthetic G oligonucleotide

<400> SEQUENCE: 1
gggggggggg                                                              10

<210> SEQ ID NO 2
<211> LENGTH: 10
<212> TYPE: DNA
<213> ORGANISM: Artificial sequence
<220> FEATURE:
<223> OTHER INFORMATION: palindromic sequence

<400> SEQUENCE: 2
gacgatcgtc                                                              10

<210> SEQ ID NO 3
<211> LENGTH: 19
<212> TYPE: DNA
<213> ORGANISM: Artificial sequence
<220> FEATURE:
<223> OTHER INFORMATION: G-rich oligonucleotide

<400> SEQUENCE: 3
ggggacgatc gtcgggggg                                                    19

<210> SEQ ID NO 4
<211> LENGTH: 20
<212> TYPE: DNA
<213> ORGANISM: Artificial sequence
<220> FEATURE:
<223> OTHER INFORMATION: G-rich oligonucleotide

<400> SEQUENCE: 4
gggggacgat cgtcggggggg                                                  20

<210> SEQ ID NO 5
<211> LENGTH: 21
<212> TYPE: DNA
<213> ORGANISM: Artificial sequence
<220> FEATURE:
<223> OTHER INFORMATION: G-rich oligonucleotide

<400> SEQUENCE: 5
ggggggacga tcgtcggggg g                                                 21

<210> SEQ ID NO 6
<211> LENGTH: 22
<212> TYPE: DNA
<213> ORGANISM: Artificial sequence
<220> FEATURE:
<223> OTHER INFORMATION: G-rich oligonucleotide

<400> SEQUENCE: 6 ggggggggacg atcgtcgggg gg                                               22

<210> SEQ ID NO 7
<211> LENGTH: 24
<212> TYPE: DNA
<213> ORGANISM: Artificial sequence

```
<220> FEATURE:
<223> OTHER INFORMATION: G-rich oligonucleotide

<400> SEQUENCE: 7
ggggggggac gatcgtcggg gggg                                              24

<210> SEQ ID NO 8
<211> LENGTH: 26
<212> TYPE: DNA
<213> ORGANISM: Artificial sequence
<220> FEATURE:
<223> OTHER INFORMATION: G-rich oligonucleotide

<400> SEQUENCE: 8 gggggggggga cgatcgtcgg gggggg                                           26

<210> SEQ ID NO 9
<211> LENGTH: 28
<212> TYPE: DNA
<213> ORGANISM: Artificial sequence
<220> FEATURE:
<223> OTHER INFORMATION: G-rich oligonucleotide

<400> SEQUENCE: 9 ggggggggggg acgatcgtcg gggggggg                                         28

<210> SEQ ID NO 10
<211> LENGTH: 30
<212> TYPE: DNA
<213> ORGANISM: Artificial sequence
<220> FEATURE:
<223> OTHER INFORMATION: G-rich oligonucleotide

<400> SEQUENCE: 10
gggggggggg gacgatcgtc gggggggggg                                        30

<210> SEQ ID NO 11
<211> LENGTH: 30
<212> TYPE: DNA
<213> ORGANISM: Artificial sequence
<220> FEATURE:
<223> OTHER INFORMATION: G-rich oligonucleotide

<400> SEQUENCE: 11
ggggggcgac gacgatcgtc gtcgggggggg                                       30
```